United States Patent [19]

Sasse et al.

[11] Patent Number: 5,292,744
[45] Date of Patent: Mar. 8, 1994

[54] 1-[PYRI(MI)DYL-(2)]-5-HYDROXY-PYRAZOLE MICROBICIDES

[75] Inventors: Klaus Sasse, Bergisch-Gladbach; Michael Schwamborn; Peter Wachtler, both of Cologne; Monika Frie, Odenthal; Georg-Wilhelm Ludwig, Krefeld; Wilfried Paulus, Krefeld; Hans-Georg Schmitt, Krefeld, all of Fed. Rep. of Germany

[73] Assignee: Bayer Aktiengesellschaft, Leverkusen, Fed. Rep. of Germany

[21] Appl. No.: 929,652

[22] Filed: Aug. 12, 1992

Related U.S. Application Data

[62] Division of Ser. No. 731,680, Jul. 17, 1991, Pat. No. 5,175,176.

[30] Foreign Application Priority Data

Jul. 24, 1990 [DE] Fed. Rep. of Germany ....... 4023488

[51] Int. Cl.$^5$ .................. A01N 43/56; A01N 43/54; C07D 401/04
[52] U.S. Cl. .................. 514/275; 514/273; 544/320; 544/321; 544/324; 544/331
[58] Field of Search .............. 544/320, 321, 324, 331; 514/275, 273

[56] References Cited

U.S. PATENT DOCUMENTS 3,040,047  6/1962  Sirakawa .................. 544/320

FOREIGN PATENT DOCUMENTS 894242  2/1972  Canada .................. 544/320
4217909  9/1967  Japan .................. 544/331

OTHER PUBLICATIONS

Matsuura et al, "1-(4-halo-6-lower alkyl-2-pyrimidinyl) etc" CA81:63663m (1974).
Dohmori et al, "Pyrimidinylpyrazoles II, Ring, etc" CA71:101805n (1969).
Naito et al, "Pyrimidinylpyrazoles, I. Synthesis, etc" CA71:101800g (1969).
Steel et al, "Heterocyclic Tautomerism. The, etc" CA100:208726g (1984).
Gocan et al, "The Optimization of Eluent, etc" CA113:78308c (1990).
Ferrer International S.A, "Pyrozole Derivatives" CA87:68412n (1977).
Hirayama et al, "1-(2-Pyrimidinyl)-pyrazolones" CA82:171017h (1974).
Konishi et al, "Fungicidal Pyrimidinylhydrazones, etc" CA113:36297t (1990).
Hirayama et al, "2-(3-Methyl-1-Pyrazolyl) etc" CA86:171491r (1977).
Hirayama et al, "Alkoxypyrazoles" CA84:180257e (1976).
Sano et al, "Pyrimidinylpyrazoles, etc" CA71:101806p (1969).
Konishi, et al., J. Pesticide Sci. 15, pp. 13-22 (1990), "Fungicidal Activity of Pyrazolylpyrimidines".

Primary Examiner—Patricia L. Morris
Attorney, Agent, or Firm—Sprung Horn Kramer & Woods

[57] ABSTRACT

The invention relates to the use of certain 1-[2-pyri(mi)-dyl]-5-hydroxy-pyrazoles which are characterized by formula (I) given in the description, as microbicides for the protection of industrial materials, and to certain novel 1-[2-pyri(mi)dyl]-5-hydroxy-pyrazoles which are characterised by formula (II) given in the description.

7 Claims, No Drawings

1-[PYRI(MI)DYL-(2)]-5-HYDROXY-PYRAZOLE MICROBICIDES

This is a division, of application Ser. No. 07/731,680, filed Jul. 17, 1991, now U.S. Pat. No. 5,175,176.

The invention relates to the use of certain 1-[2-pyri(mi)dyl]-5-hydroxy-pyrazoles as microbicides for the protection of industrial materials, and to certain novel 1-[2-pyri(mi)dyl]-5-hydroxy-pyrazoles.

U.S. Pat. No. 4,663,327 discloses 1-hetaryl-4-aryl-pyrazolin-5-ones, for example 1-[2-pyri(mi)dyl]-4-phenyl-pyrazolin-5-ones, and their microbicidal properties. However, since the compounds are coloured and result in discolourations when incorporated into industrial materials, for example paints and plastics, they cannot be used in the protection of materials in spite of their good microbicidal properties.

In Japanese Application JA-A 62/149,617 (CA Vol. 108, 11 247 k) which has been published, there are furthermore described 1-hetaryl-pyrazolin-5-ones, for example 1-[2-pyri(mi)dyl]-pyrazolin-5-ones, and their use as pharmaceuticals.

Other compounds which are still used to date for imparting fungicidal properties to plastics are organoarsenic compounds, even though the replacement of these compounds and also of the organomercury compounds which are still used in paints is highly desirable for ecotoxicological reasons. However, no ecotoxicologically more favourable compounds have been found to date which meet the high demands which must be made of microbicides which can be used for imparting microbicidal properties to plastics. Indeed, such microbicides must have resistance to high temperatures, besides a good microbicidal activity, and must furthermore not adversely affect the properties of the plastics.

It has now been found that 1-[2-pyri(mi)dyl]-5-hydroxy-pyrazoles of a particular formula have a microbicidal action in plastics and paints which equals that of the organoarsenic and organomercury compounds and which furthermore have the required thermal stability and which moreover meet the demands of being ecotoxicologically acceptable and do not adversely affect the properties, for example colour and elasticity, of the plastics, paints and coatings to which these compounds have been added.

The invention therefore relates to the use of 1-[2-pyri(mi)dyl]-5-hydroxy-pyrazoles of the formula

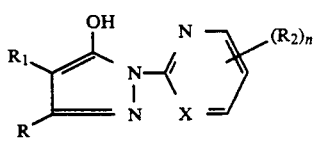

in which
R represents hydrogen, or an optionally substituted alkyl, aralkyl or alkoxy group,
$R_1$ represents hydrogen, an optionally substituted alkyl, alkenyl, alkinyl, cycloalkyl, aralkyl, alkoxy, alkylmercapto, aralkoxy, aralkylmercapto, aryloxy, arylmercapto, alkoxycarbonyl or aminocarbonyl group, or $R_1$ together with R forms a divalent alk(en)ylene radical which has 3 to 6 C atoms in the chain,
$R_2$ represents halogen, nitro, cyano or an optionally substituted alkyl, alkoxy, alkylmercapto, alkoxycarbonyl or aminocarbonyl group,
n represents zero or an integer from 1 to 3, where $R_2$ can represent identical or different radicals when n is 2 or 3, and
X represents CH or N,
as microbicides for the protection of industrial materials.

Preferably used 1-[2-pyri(mi)dyl]-5-hydroxy-pyrazoles of the formula (I) are those in which
X has the meaning given under formula (I),
n is zero,
R represents hydrogen, alkyl or aralkyl, and
$R_1$ represents hydrogen, optionally substituted alkyl, cycloalkyl, aralkyl, alkoxy, aralkylmercapto or alkoxycarbonyl.

Particularly preferred 1-[2-pyri(mi)dyl]-5-hydroxy-pyrazoles of the formula (I) are those in which
X has the meaning given under formula (I),
n is zero,
R represents hydrogen, $C_6$-$C_{12}$-alkyl or benzyl, and
$R_1$ represents hydrogen, $C_1$-$C_8$-alkyl, $C_5$-$C_7$-cycloalkyl, $C_1$-$C_6$-alkoxy, optionally substituted -benzyl, $C_1$-$C_6$-alkoxycarbonyl or benzylmercapto.

Very particularly preferred are the 1-[2-pyri(mi)dyl]-5-hydroxy-pyrazoles of the formula (I) when, in this formula,
X represents CH,
n is zero,
R represents hydrogen, and
$R_1$ represents $C_1$-$C_4$-alkyl, benzyl, chlorobenzyl or ethoxycarbonyl.

Novel compounds from amongst the 1-[2-pyri(mi)dyl]-5-hydroxy-pyrazoles to be used according to the invention are those of the formula (II).

The invention therefore also relates to novel 1-[pyri(mi)dyl]-5-hydroxy-pyrazoles of the formula

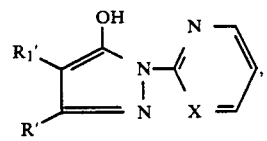

in which
X represents CH or N,
R' represents hydrogen, or an optionally substituted $C_6$-$C_{10}$-alkyl, aralkyl or alkoxy group, and
$R_1'$ represents hydrogen, an optionally substituted $C_6$-$C_{12}$-alkyl, alkenyl, alkinyl, cycloalkyl, aralkyl, alkoxy, alkylmercapto, aralkoxy, aralkylmercapto, aryloxy, arylmercapto, alkoxycarbonyl or aminocarbonyl group, or $R_1'$ together with R' forms a divalent alk(en)ylene radical which has 3 to 6 C atoms in the chain,
with the proviso that R' and $R_1'$ do not simultaneously represent hydrogen.

Typical representatives of the pyrazoles of the formula (I) which can be used according to the invention and of the pyrazoles of the formula (II) according to the invention are listed in the examples.

The pyrazoles of the formula (I) which are to be used according to the invention and the novel pyrazoles of the formula (II) according to the invention can also exist in their tautomeric pyrazolin-5-one form.

The following may be mentioned as optionally substituted alkyl radicals for R and $R_1$: $C_1-C_{12}$-alkyl groups such as methyl, ethyl, n- and i-propyl, n-butyl, i-pentyl, hexyl, i-octyl, n-decyl and n-dodecyl; suitable substituents for these alkyl radicals are mainly halogen atoms, preferably chlorine or fluorine, furthermore $C_1-C_4$-alkoxy and $C_1-C_6$-alkoxycarbonyl groups. Examples of representatives of the substituted alkyl radicals are the difluoromethyl, trifluoromethyl and monochlorodifluoromethyl radical, furthermore the methoxymethyl and the methoxycarbonylmethyl and the ethoxycarbonylmethyl radical.

The following may be mentioned for R, $R_1$, R' and $R_1'$:

As optionally substituted aralkyl groups, the benzyl, α-methylbenzyl, α,α-dimethylbenzyl, 2-phenylethyl and the α- and β-naphthylmethyl radical, and benzyl radicals which are substituted by halogen, in particular chlorine and fluorine, $C_1-C_4$-alkyl, in particular methyl, ethyl, trifluoromethyl, difluorochloromethyl, difluoromethyl and trichloromethyl, and by $C_1-C_4$-alkoxy, in particular methoxy, ethoxy, trifluoromethoxy, difluorochloromethoxy and difluoromethoxy, $C_1-C_4$-alkylmercapto such as methylmercapto, trifluoromethylmercapto, difluorochloromethylmercapto, nitro and/or cyano.

As optionally substituted alkoxy groups: $C_1-C_{12}$-alkoxy groups such as the methoxy, ethoxy, butoxy and hexoxy group.

The following may be mentioned for $R_1$ and $R_1'$:

As an optionally substituted alkenyl group, the allyl group;

as optionally substituted alkinyl groups, the propinyl, 1-iodo-propinyl and the 3,3-dimethylpropinyl group;

as optionally substituted cycloalkyl groups, $C_5-C_7$-cycloalkyl groups, in particular cyclohexyl radicals which are substituted by $C_1-C_4$-alkyl groups or by halogen, such as the cyclohexyl radical, the methylcyclohexyl, the dimethylcyclohexyl and the 1,3,3-trimethylcyclohexyl and the 3-chlorocyclohexyl radical;

as optionally substituted alkylmercapto groups, $C_1-C_2$-alkylmercapto groups which are substituted by halogen, such as the methylmercapto, trifluoromethylmercapto, difluoromethylmercapto and the difluorochloromethylmercapto group;

as aralkoxy groups, the benzyloxy group and benzyloxy groups which are substituted by halogen and $C_1-C_4$-alkyl radicals;

as aralkylmercapto groups, the benzylmercapto group and the benzylmercapto groups which are substituted by halogen and/or $C_1-C_4$-alkyl;

as aryloxy groups, the phenoxy group and phenoxy groups which are substituted by halogen, $C_1-C_4$-alkyl, $C_1-C_2$-halogenoalkyl, cyano, nitro, trifluoromethyl and difluoromethyl;

as arylmercapto groups, the phenylmercapto group and the phenylmercapto groups which are substituted by halogen, $C_1-C_4$-alkyl, $C_1-C_2$-halogenoalkyl, cyano and nitro;

as alkoxycarbonyl groups, $C_1-C_6$-alkoxycarbonyl groups, such as the methoxycarbonyl and ethoxycarbonyl group; as aminocarbonyl group, the carboxamido, N-methylcarboxamido and N,N-dimethylaminocarboxamido group;

as alk(en)ylene radicals which have 3 to 6 C atoms in the chain, the ethylene, 1,3-propylene, 1,4-butylene and the 1,4-butadiene-(1,4)ylene radical.

Optionally substituted alkyl radicals for $R_2$ which may be mentioned are $C_1-C_4$-alkyl and $C_1-C_2$-halogenoalkyl radicals, such as the methyl, trifluoromethyl, difluoromethyl and difluorochloromethyl radical.

The pyrazoles of the formula (I) which are to be used according to the invention and the novel pyrazolines of the formula (II) according to the invention can be prepared by condensation reactions which are known per se, for example those described in Chem. Ber. 38 (1905) 2104; Bull. Soc. Chim. France 1967, 3780–92. These condensation reactions proceed following the reaction scheme below:

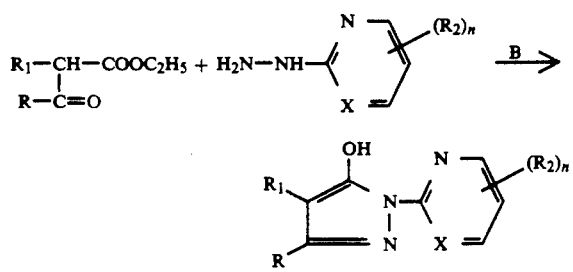

If appropriate, the condensation can be carried out in the presence of a solvent; solvents which have proved suitable are mainly alcohols, such as ethanol, or aromatic hydrocarbons, such as toluene.

To facilitate the cyclisation reaction, it is advantageous to add bases, such as sodium hydroxide, potassium hydroxide or potassium tert.-butylate.

The condensation reaction can be carried out within a substantial temperature range. Hydrazone formation, which proceeds first, can be carried out at temperatures from 20° to 110° C., preferably between 60° and 90° C. The cyclo-condensation reaction, which proceeds after the base has been added, can be effected at temperatures from 20° to 100°, preferably 20° to 40° C. Since the addition of bases proceeds exothermally in some cases, cooling may be necessary in this reaction step.

The 1-[2-pyri(mi)dyl]-5-hydroxy-pyrazoles are isolated from the reaction mixtures using known methods. In general, a procedure is followed in which the reaction mixtures are freed from the solvent and the residue is treated with aqueous hydrochloric acid. The pyrazoles which precipitate during this process are separated off by filtration by suction. However, it is also possible to pour the reaction mixture directly into a large excess of dilute hydrochloric acid and to filter off the pyrazoles which separate out as a precipitate.

The starting compounds required for the condensation reaction, optionally α-substituted β-ketocarboxylic esters or α-formylcarboxylic esters and 2-hydrazinopyri(mi)dines, are either known compounds or can be prepared analogously to known compounds by above-described processes.

The industrial materials to be protected according to the invention are non-living materials which have been prepared for use in industry. For example, industrial materials which are intended to be protected by active compounds according to the invention from microbial change or destruction can be glues, sizes, paper and board, textiles, leather, wood, paints, plastics and plastic articles, cooling lubricants and other materials which can be infested with, or destroyed by, microorganisms. Parts of production plants, for example cooling-water circuits, whose function may be impaired by the multiplication of microorganisms, may also be mentioned within the scope of the materials to be protected. Industrial materials which may be mentioned within the scope of the present invention are preferably paints, plastics and plastic articles.

Microorganisms, capable of bringing about degradation of, or change in, the industrial materials, which may be mentioned are, for example, bacteria, fungi, yeasts, algae and slime organisms. The active compounds according to the invention preferably act against fungi, in particular moulds, and against fungi which discolour and destroy wood permanently.

Microorganisms of the following genera may be mentioned as examples:
Alternaria, such as *Alternaria tenuis*,
Aspergillus, such as *Aspergillus niger*,
Chaetomium, such as *Chaetomium globosum*,
Coniophora, such as *Coniophora puteana*,
Lentinus, such as *Lentinus tigrinus*,
Penicillium, such as *Penicillium glaucum*,
Polyporus, such as *Polyporus versecolor*,
Aureobasidium, such as *Aureobasidium pullulans*,
Sclerophoma, such as *Sclerophoma pityophila*,
Trichoderma, such as *Trichoderma viride*,
Escherichia, such as *Escherichia coli*,
Pseudomonas, such as *Pseudomonas aeruginosa*,
Staphylococcus, such as *Staphylococcus aureus*.

Depending on the field of application, the active compounds which are to be used according to the invention can be converted into the customary formulations, such as solutions, emulsions, suspensions, powders, pastes and granules.

These can be prepared in a manner known per se, for example by mixing the active compounds with an extender which consists of liquid solvent and/or solid carriers, optionally with the use of surface-active agents, such as emulsifiers and/or dispersants, it being possible, if appropriate, for organic solvents such as alcohols to be used as auxiliary solvents in the event that water is used as the extender.

Liquid solvents for the active compounds can be, for example, water, alcohols, such as lower aliphatic alcohols, preferably ethanol or isopropanol, or benzyl alcohol, ketones, such as acetone or methyl ethyl ketone, liquid hydrocarbons, such as petroleum fractions, or halogenated hydrocarbons, such as 1,2-dichloroethane.

The microbicidal agents used for the protection of industrial materials contain the active compounds in general in an amount from 1 to 100% by weight, preferably from 10 to 90% by weight.

The use concentrations of the active compounds which are to be used according to the invention depend on the nature and the occurrence of the microorganisms to be controlled, and on the composition of the material to be protected. The optimum amount for use can be determined by serial tests. In general, the use concentrations are in the range from 0.001 to 5% by weight, preferably from 0.05 to 1.0% by weight, relative to the material to be protected.

The active compounds which are to be used according to the invention can also be used as a mixture with other known active compounds. The following active compounds may be mentioned by way of example: benzyl alcohol mono(poly)hemiformal and other formaldehyde-releasing compounds, benzimidazolylmethylcarbamates, tetramethylthiuram disulphide, zinc salts of dialkyldithiocarbamates, 2,4,5,6-tetrachloroisophthalonitrile, thiazolylbenzimidazole, mercaptobenzothiazole, 2-thiocyanatomethylthiobenzothiazole, methylene bisthiocyanate, and phenol derivatives such as 2-phenylphenol, (2,2'-dihydroxy-5,5'-dichloro)-diphenylmethane and 3-methyl-4-chlorophenol, organotin compounds, N-trihalogenomethylthio compounds, such as folpet, fluorofolpet and dichlofluanid, azole fungicides such as triadimefon, triadimenol and bitertanol, tebuconazole, propiconazole and prochloraz, and also iodopropargyl compounds such as jodpropargylbutyl-carbamat.

Moreover, the active compounds according to the invention in particular those of the examples listed, can be present as a mixture with other active compounds, such as insecticides, attractants, sterilants, acaricides, nematicides, fungicides, growth-regulating substances or herbicides, in their commercially available formulations and in the use forms prepared from these formulations.

The insecticides include, for example, phosphates, carbamates, carboxylates, formamidines, tin compounds, substances produced by microorganisms, etc. Preferred components for mixtures are the following:

1. From the group of the phosphates
azinphos-ethyl, azinphos-methyl, 1-(4-chlorophenyl)-4-(O-ethyl, S-propyl)phosphoryloxypyrazole (TIA-230), chlorpyrifos, coumaphos, demeton, demeton-S-methyl, diazinon, dichlorvos, dimethoate, ethoprophos, etrimfos, fenitrothion, fenthion, heptenophos, parathion, parathion-methyl, phosalone, pirimiphosethyl, pirimiphosmethyl, profenofos, prothiofos, sulprofos, triazophos and trichlorphon.

2. From the group of the carbamates
aldicarb, bendiocarb, BPMC (2-(1-methylpropyl)-phenylmethylcarbamate), butocarboxim, butoxicarboxim, carbaryl, carbofuran, carbosulfan, cloethocarb, isoprocarb, methomyl, oxamyl, pirimicarb, promecarb, propoxur and thiodicarb.

3. From the group of the carboxylic esters
allethrin, alphamethrin, bioallethrin, bioresmethrin, cycloprothrin, cyfluthrin, cyhalothrin, cypermethrin, deltamethrin, alpha-cyano-3-phenyl-2-methylbenzyl 2,2-dimethyl-3-(2-chloro-2-trifluoromethylvinyl)cycloprop anecarboxylate (FMC 54800), fenpropathrin, fenfluthrin, fenvalerate, flucythrinate, flumethrin, fluvalinate, permethrin, resmethrin, tralomethrin.

4. From the group of the formamidines
amitraz and chlordimeform

5. From the group of the tin compounds
azocyclotin, cyhexatin and fenbutatin oxide 6. Others
abamectin, Bacillus thuringiensis, bensultap, binapacryl, bromopropylate, buprofecin, camphechlor, cartap, chlorobenzilate, chlorfluazuron, 2-(4-chlorophenyl)-4,5-diphenylthiophene (UBI-T 930), chlofentezine, 2-naphthylmethyl cyclopropanecarboxylate (Ro 12-0470), cyromacin, DDT, dicofol, N-(3,5-dichloro-4-(1,1,2,2-tetrafluoroethoxy)phenylamino)carbonyl)-2,6-difluorobenzamide (XRD 473), diflubenzuron, N-(2,3-dihydro-3-methyl-1,3-thiazol-2-ylidene)2,4-xylidine, dinobuton, dinocap, endosulfan, fenoxycarb, fenthiocarb, flubenzimine, flufenoxuron, gamma-HCH, hexythiazox, hydramethylnon (AC 217 300), ivermectin, 2-nitromethyl-4,5-dihydro-6H-thiazine (SD 52618), 2-nitromethyl-3,4-dihydrothiazole (SD 35651), 2-nitromethylene-1,3-thiazinan-3-yl-carbamaldehyde (WL 108 477), propargite, teflubenzuron, tetradifon, tetrasul, thiocyclam, triflumaron, and nuclear polyhedrosis and granulosis viruses.

EXAMPLES

Example 1

A mixture of 7.2 g of ethyl propionylacetate, 5.4 g of 2-hydrazinopyridine and 200 ml of ethanol is refluxed for 3 hours, with stirring. The reaction mixture is then cooled to 20° to 30° C., and, with stirring, treated with 5.8 g of potassium tert.-butylate. After the mixture has been stirred for 10 hours, the solvent is removed in vacuo, the residue is treated with 200 ml of water, and a pH of 1 is established by adding hydrochloric acid. The precipitate is filtered off with suction, dried, and then recrystallised from alcohol.

5.2 g (=55.1% of theory) of 1-[2-pyridyl]-3-ethyl-5-hydroxy-pyrazole are obtained. M.p.: 189° C.

The 3-substituted 1-[pyri(mi)dyl-(2)]-5-hydroxy-pyrazoles listed in Table 1 below were obtained in the same manner from the corresponding ethyl acylacetates.

The pyrazoles, which were obtained in the form of oils, were characterised by the δ-value of the pyrazole H, determined by NMR.

TABLE 1

| Example | R (R$_1$, R$_2$ = H) | X | Physical characteristics |
| --- | --- | --- | --- |
| 2 | CH$_3$ | N | δ = 5.38 ppm |
| 3 | CF$_3$ | CH | δ = 5.85 ppm |
| 4 | t-butyl | CH | δ = 5.47 ppm |
| 5 | CH$_3$OCH$_2$ | CH | δ = 5.57 ppm |
| 6 | iC$_3$H$_7$ | CH | δ = 5.42 ppm |
| 7 | C$_8$H$_{14}$ | CH | δ = 5.42 ppm |
| 8 | C$_{10}$H$_{21}$ | CH | δ = 5.42 ppm |
| 9 | phenyl | CH | δ = 5.92 ppm |
| 10 | 3,4-dichlorophenyl | CH | m.p. = 124–125° C. |
| 11 | 4-nitrophenyl | CH | δ = 5.96 ppm |
| 12 | 4-methoxyphenyl | CH | δ = 6.06 ppm |
| 13 | 3,4-dimethoxyphenyl | CH | δ = 6.06 ppm |
| 14 | benzyl | CH | δ = 5.32 ppm |
| 15 | CH$_3$— | N | M$^\oplus$ = 176 |
| 16 | phenyl | N | m.p. = 146–49° C. |

Example 17

A mixture of 24.9 g of ethyl α-formyl-octanoate (73%), 9.8 g of 2-hydrazinopyridine and 200 ml of ethanol is refluxed for 3 hours, with stirring. The reaction mixture is then cooled to 20° to 30° C. and, with stirring, treated with 10.4 g of potassium tert.-butylate, in portions. After the mixture has been stirred for 10 hours, the solvent is removed in vacuo. The residue is treated with 200 ml of water, and a pH of 1 is established using hydrochloric acid. The oil which separates out is extracted using methylene chloride. After the methylene chloride solution has been dried over sodium sulphate, the solvent is removed in vacuo.

12.1 g (=54.8% of theory) of 1-[2-pyridyl]-4-hexyl-5-hydroxy-pyrazole are obtained in the form of a yellow oil which crystallises slowly. M.p.: 37°–38° C.

The 4-substituted 1-[pyri(mi)dyl-(2)]-5-hydroxy-pyrazoles which are listed in Table 2 below were obtained in the same manner from the corresponding ethyl α-formylcarboxylates.

TABLE 2

| Example | R$_1$ (R, R$_2$ = H) | X | Physical characteristics |
| --- | --- | --- | --- |
| 18 | CH$_3$ | CH | δ = 7.35 ppm |
| 19 | C$_2$H$_5$ | CH | δ = 7.35 ppm |
| 20 | i-C$_3$H$_7$ | CH | δ = 7.48 ppm |
| 21 | n-C$_4$H$_9$ | CH | δ = 7.36 ppm |
| 22 | C$_{10}$H$_{21}$ | CH | δ = 7.50 ppm |
| 23 | i-C$_5$H$_{11}$ | CH | δ = 7.52 ppm |
| 24 | CH$_3$ | N | δ = 7.51 ppm |
| 25 | C$_2$H$_5$ | N | δ = 7.50 ppm |
| 26 | n-C$_4$H$_9$ | N | δ = 7.41 ppm |
| 27 | benzyl | —CH | δ = 7.35 ppm |

TABLE 2-continued
| Example | R₁ (R, R₂ = H) | X | Physical characteristics |
|---|---|---|---|
| 28 | 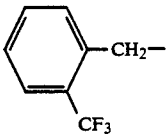 | —CH | δ = 7.33 ppm |
| 29 | 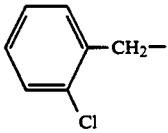 | —CH | δ = 7.30 ppm |
| 30 | 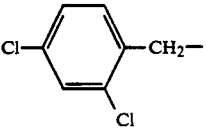 | —CH | δ = 7.28 ppm |
| 31 | 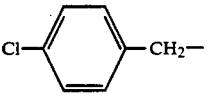 | —CH | δ = 7.32 ppm |
| 32 | 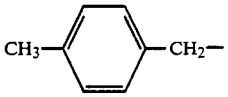 | —CH | δ = 7.33 ppm |
| 33 |  | CH | m.p.: 70–71° C. |
| 34 | 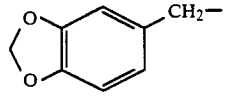 | CH | m.p.: 156–157° C. |
| 35 | 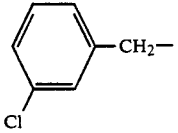 | CH | m.p.: 67–68° C. |
| 36 | 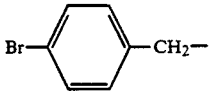 | CH | δ = 7.28 ppm |
| 37 | 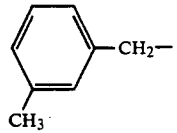 | CH | m.p.: 60–61° C. |
| 38 | 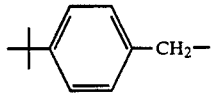 | CH | δ = 7.22 ppm |
| 39 | 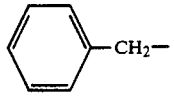 | N | m.p.: 110° C. |

TABLE 2-continued

| Example | R₁ (R, R₂ = H) | X | Physical characteristics |
|---|---|---|---|
| 40 | 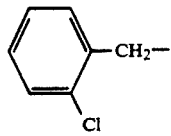 2-Cl-C₆H₄-CH₂— | N | δ = 7.50 ppm |
| 41 | 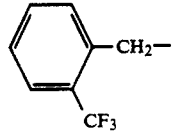 2-CF₃-C₆H₄-CH₂— | N | δ = 7.42 ppm |
| 42 | 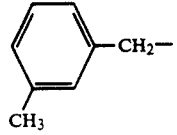 3-CH₃-C₆H₄-CH₂— | N | m.p.: 110–12° C. |
| 43 | 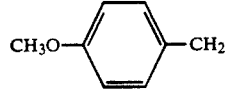 CH₃O-C₆H₄-CH₂— | N | m.p.: 102–103° C. |
| 44 | 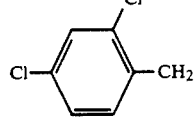 2,4-Cl₂-C₆H₃-CH₂— | N | m.p.: 192–94° C. |
| 45 | 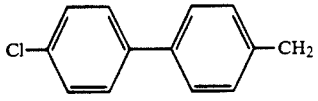 4-Cl-C₆H₄-C₆H₄-CH₂— | N | δ = 7.37 ppm |
| 46 | CH₃OC(O)— | CH | δ = 7.86 ppm |
| 47 | C₂H₅OC(O)— | CH | δ = 7.84 ppm |
| 48 | C₃H₇C(O)— | CH | δ = 7.85 ppm |
| 49 | t-C₄H₉C(O)— | CH | δ = 7.70 ppm |
| 50 | C₈H₁₇OC(O)— | CH | δ = 7.87 ppm |
| 51 | C₂H₅OCO— | N | m.p.: 155–58° C. |
| 52 | C₂H₅OCO—CH₂— | C | δ = 7.61 ppm |
| 53 | n-C₄H₉OCO—CH₂— | C | δ = 7.50 ppm |
| 54 | n-C₆H₁₃OCO—CH₂ | C | δ = 7.59 ppm |
| 55 | i-C₄H₉OCO—CH₂ | C | δ = 7.86 ppm |
| 56 | C₈H₁₇OCO—CH₂ | C | δ = 7.45 ppm |
| 57 | C₂H₅NH—CO—CH₂— | C | δ = 7.42 ppm |
| 58 | C₂H₅OCO—CH₂— | N | δ = 7.62 ppm |
| 59 | C₆H₁₃—S | CH | δ = 7.30 ppm |
| 60 | 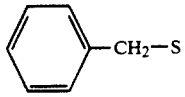 C₆H₅-CH₂-S | CH | δ = 7.20 ppm |

TABLE 2-continued

| Example | R₁ (R, R₂ = H) | X | Physical characteristics |
|---|---|---|---|
| 61 | CH₃O— | CH | δ = 7.38 ppm |
| 62 | C₄H₉O— | CH | δ = 7.32 ppm |
| 63 | CH₂=CH—CH₂— | CH | δ = 7.35 ppm |
| 64 | 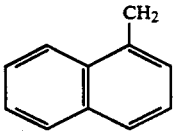 (naphthyl-CH₂) | CH | δ = 7.47 ppm |

Example 65

A mixture of 14.1 g of ethyl α-benzyl-benzoylacetate, 5.5 g of hydrazinopyridine and 100 ml of ethanol is refluxed for 3 hours, with stirring. The reaction mixture is then cooled to 20° to 30° C. and, with stirring, treated with 5.6 g of potassium tert.-butylate, in portions. The reaction mixture is stirred for 15 hours at 20° to 30° C. The solvent is subsequently removed in vacuo. The residue is treated with 200 ml of water, and a pH of 1 is established using hydrochloric acid. The precipitate is filtered off with suction and stirred with isopropanol.

10 g (=61.1% of theory) of 2-[2-pyridyl]-3-phenyl-4-benzyl-5-hydroxy-pyrazole are obtained. M.p.: 115°–116° C.

The 3- and 4-substituted 1-[2-pyri(mi)dyl]-5-hydroxy-pyrazoles which are given in Table 3 below were obtained in the same manner from the correspondingly substituted ethyl acylacetates.

TABLE 3

| Example | R | R₁ (R₂ = H) | X | M.p. (°C.) |
|---|---|---|---|---|
| 66 | CH₃ | CH₃ | CH | 123.5-26° C. |
| 67 | C₂H₅ | CH₃ | CH | 50-53 |
| 68 | i-C₃H₇ | CH₃ | CH | 71-72 |
| 69 | CH₃ | C₂H₅ | CH | 107-08 |
| 70 | CH₃ | n-C₄H₉ | CH | 94-97 |
| 71 | CH₃ | n-C₆H₁₃ | CH | 42-43 |
| 72 | CH₃ | n-C₇H₁₅ | CH | 39-40 |
| 73 | CH₃ | C₁₂H₂₅ | CH | 47-48 |
| 74 | CH₃ | cyclohexyl-H | CH | 82-83 |
| 75 | CH₃ | C₆H₅—O—(CH₂)₂— | CH | 121-24 |
| 76 | CH₃ | C₆H₅—O—(CH₂)₃— | CH | 84-87 |
| 77 | CH₃ | HC≡C—C(CH₃)₂— | CH | 57-59 |
| 78 | CH₃ | C₆H₅— | CH | 114-15 |
| 79 | CH₃ | C₆H₅—CH₂— | CH | 56-63 |
| 80 | CH₃ | C₆H₅—CH(CH₃)— | CH | 62-64 |
| 81 | CH₃ | biphenyl | CH | 153-54 |

TABLE 3-continued

| Example | R | $R_1$ ($R_2$ = H) | X | M.p. (°C.) |
|---|---|---|---|---|
| 82 | $R + R_1 =$ | $(CH_2)_4$ | CH | 125–26 |
| 83 | $R + R_1 =$ | $(CH_2)_5$ | CH | 108–10 |
| 84 | $CH_3$ | $C_2H_5$ | N | 111–13 |
| 85 | $C_2H_5$ | $CH_3$ | N | 109–12 |
| 86 | $i\text{-}C_3H_7$ | $CH_3$ | N | 84–86 |
| 87 | $CH_3$ | $n\text{-}C_4H_9$ | N | 88–89 |
| 88 | $CH_3$ | $n\text{-}C_7H_{15}$ | N | 63–65 |
| 89 | $CH_3$ | $n\text{-}C_{12}H_{25}$ | N | 73–75 |
| 90 | $CH_3$ | Ph–O–(CH$_2$)$_2$– | N | 121–24 |
| 91 | $CH_3$ | HC≡C–C(CH$_3$)$_2$– | N | 108–11 |
| 92 | $CH_3$ | Ph–CH$_2$– | N | 78–83 |
| 93 | C$_6$H$_{11}$ (cyclohexyl) | Ph–CH$_2$– | N | 155–61 |
| 94 | $CH_3$ | 4-biphenyl–CH$_2$– | N | 198–201 |
| 95 | $CH_3$ | Ph–CH(CH$_3$)– | N | 86–87 |
| 96 | $R + R_1 =$ | $(CH_2)_4$ | N | 192–96 |
| 97 | $C_2H_5$ | 5-Cl—, 6-CH$_3$—NH—, | N | 172 |
| 98 | $C_2H_5$ | 5-Br | CH | 119 |
| 99 | $C_2H_5$ | 6-CH$_3$ | CH | δ(pyrazole H) = 7.37 ppm |
| 100 | $C_6H_{13}$ | 4-CF$_3$, 6-CH$_3$ | CH | δ(pyrazole H) = 7.38 ppm |
| 101 | $C_6H_{13}$ | 6-CH$_3$ | CH | δ(pyrazole H) = 7.34 ppm |
| 102 | $C_6H_{13}$ | 5-Cl, 6-CH$_3$NH— | N | δ(pyrazole H) = 7.45 ppm |
| 103 | $C_8H_{17}$ | 5-Cl | CH | 109 |
| 104 | Ph–CH$_2$– | 4-Cl, 6-CH$_3$ | CH | 80 |
| 105 | Ph–CH$_2$– | 6-CH$_3$ | CH | δ(pyrazole H) = 7.31 ppm |
| 106 | Ph–CH$_2$– | 6-Cl | CH | 167–168 |

TABLE 3-continued

| Example | R | R₁ (R₂ = H) | X | M.p. (°C.) |
|---|---|---|---|---|
| 107 | phenyl-CH₂ | 5-Br | CH | 143 |
| 108 | phenyl-CH₂ | 5-NO₂ | CH | 170 |

USE EXAMPLES

Example A

In order to demonstrate the effectiveness against fungi, the minimum inhibitory concentrations (MICs) of the active compounds according to the invention were determined:

Active compounds according to the invention are added at concentrations from 0.1 mg/l to 5000 mg/l to an agar which is prepared from brewer's wort and peptone. When the agar has solidified, it is contaminated with pure-breed cultures of the test organisms listed in the table. The cultures are stored for 2 weeks at 28° C. and 60 to 70% relative atmospheric humidity, and the MIC is then determined MIC is the lowest concentration of active compound at which no growth whatsoever by the microbe species used takes place; it is given in Table 4 below.

sample remains free from fungus or shows not more than a slight infestation at the edge.

For contamination, fungal spores of the following nine moulds are used, these moulds being known as paint destructants or being found frequently on paints:
1. *Alternaria tenuis*
2. *Aspergillus flavus*
3. *Aspergillus niger*
5. *Cladosporium herbarum*
6. *Paecilomyces variotii*
7. *Penicillium citrinum*
8. *Aureobasidium pullulans*
9 *Stachybotrys atra Corda*

0 to 2% by weight, relative to the total solids content of the paint of the compound to be tested for its fungicidal activity, were incorporated into samples of a commercially available dispersion paint based on polyvinyl acetate. In this test, even those samples which only

TABLE 4

MIC values of various 1-[pyri(mi)dyl-(2)]-5-hydroxy-pyrazoles on fungi, indicated in mg/l

| Test organisms | 1-[Pyri(mi)dyl-(2)]-5-hydroxy-pyrazoles of Example | | | | | | | | | |
|---|---|---|---|---|---|---|---|---|---|---|
|  | 21 | 19 | 26 | 27 | 39 | 40 | 41 | 35 | 31 | 36 |
| *Alternaria tenuis* | 5 | 50 | 25 | 50 | 20 | 20 | 20 | 35 | 50 | 10 |
| *Aspergillus niger* | 2 | 10 | 50 | 20 | 50 | 50 | 50 | 20 | 50 | 20 |
| *Aureobasidium pullulans* | 35 | 50 | 20 | 20 | 10 | 35 | 35 | 50 | 35 | 20 |
| *Chaetomium globosum* | 5 | 2 | 20 | 50 | 50 | 20 | 20 | 50 | 50 | 50 |
| *Cladosporium cladosporioides* | 10 | 5 | — | — | — | — | — | — | — | — |
| *Cladosporium herbarum* | — | — | 50 | 50 | 50 | 15 | 15 | 50 | 35 | 35 |
| *Lentinus tigrinus* | 1 | 2 | 75 | 50 | 75 | 100 | 100 | 50 | 50 | 50 |
| *Penicillium glaucum* | 2 | 20 | — | — | — | — | — | — | — | — |
| *Penicillium breviante* | — | — | 50 | 100 | 50 | 20 | 20 | — | 20 | 20 |
| *Sclerophoma pityophila* | 7.5 | 2 | 50 | 5 | 20 | 35 | 35 | 20 | 75 | 10 |
| *Trichoderma viride* | 200 | 200 | 50 | 75 | 50 | 50 | 50 | 100 | 100 | 50 |

Example B (Fungicidal Action in Paints)

The fungicidal action in paints is determined by testing the coatings obtained with the paints for resistance to moulds.

The test is carried out following Report 219 of the Defence Standards Laboratories Maribyrnong/Australia as follows:

A suitable substrate is painted on both sides with the paint to be tested.

To obtain results which are relevant to practice, some of the samples are treated with a warm stream of fresh air before being tested for resistance to mould (7 days; 40° C.).

The samples which have been prepared in this manner are placed on an agar medium. Sample and medium are contaminated with fungal spores. The items are stored at 29±1° C. and 80 to 90% relative atmospheric humidity for 1 to 3 weeks, and samples are then taken. The coating is permanently mould-resistant when the contained 0.3% by weight, relative to the total solids content of the paint, of 1-(2-pyridyl)-4-ethyl-5-hydroxy-pyrazole, described in Example 19, gave permanently mould-resistant paints.

Example C (Action against microorganisms of plastics to which fungicidal properties have been imparted according to the invention)

The action which the plastics to which fungicidal properties have been imparted according to the invention take against microorganisms (various genera of fungi) was determined in accordance with Swiss Testing Procedure SNV No. 195,921 (1976; "Testing the antimycotic action of finished textiles and other materials with the aid of the agar diffusion test").

To carry out the determination, test samples (discs; diameter: 3 cm; thickness depending on the plastic to be tested 250 μm to 5 mm) of the plastics to which fungicidal properties had been imparted and, as a control, of the corresponding plain plastics were placed on 2-layer nutrient agar plates which had been inoculated with spores or hyphae of the test organism in question. The plates were incubated for 4 weeks at 29±1° C. Fungal growth on the test samples and in the contact zone under the test-samples was then determined visually and, in the event that an inhibition zone had formed under the test samples, the size of this inhibition zone was measured.

Inhibition zone is understood as meaning the zone which is free from fungi, calculated using the following formula:

$$H = \frac{D-d}{2},$$

in which
H = inhibition zone [mm]
D = total diameter of test sample and inhibition zone [mm];
d = diameter of the test sample [mm].

Table 5 which follows gives the results, fungal growth and sizes of the inhibition zones, which were obtained when the amounts indicated in the table of the compounds also indicated in the table were used in the plastics also indicated in the table, when the tests were evaluated.

TABLE 5

Action against various test organisms of the plastics to which fungicidal properties have been imparted Test Organisms used:
(a) *Aspergillus niger*
(b) *Aspergillus terreus*
(c) *Chaetomium globosum*
(d) *Trichoderma viride*
(e) *Cladosporium herbarium*
(f) *Streptoverticilium reticulum*

The abbreviations denote:
H = inhibition zone [mm]
PB = fungal growth (4 scores: none, slight, medium, total)

| Compound used as fungicide, in accordance with Example | Amount used [g/100 g of plastic] | (a) H/PB | (b) H/PB | (c) H/PB | (d) H/PB | (e) H/PB | (f) H/PB |
|---|---|---|---|---|---|---|---|
| 47 | 1.0/polyvinyl chloride | 0/ medium | 0/ slight | 0/ slight | 0/ slight | 0-6 none | >25/ none |
| 19 | 1.0/polyvinyl chloride | 20-25/ none | >25/ none | >25/ none | 0/ slight | 12-15 none | 8-11/ none |
| 18 | 1.0/polyvinyl chloride | 0/ slight | >25/ none | >25/ none | 0/ slight | 15-18/ none | 6-9/ none |
| 27 | 0.5/polyvinyl chloride | 3-5/ none | 1-2/ none | 1-2/ none | 0/ medium | 1-3/ none | 8-10/ none |
| Control | 0/polyvinyl chloride | 0/ total | 0/ total | 0/ total | 0/ total | 0/ total | 0/ total |
| 19 | 0.15/polyurethane | 4-6/ none | 2-4/ none | 0-1/ none | 10-12/ none | 8-10/ none | 15-20/ none |
| Control | 0/polyurethane | 0/ total | 0/ total | 0/ total | 0/ total | 0/ total | 0/ total |

Polyvinyl chloride = PVC pastes (emulsion PVC)
Polyurethane = polyester polyurethane (Bayflex ®)

We claim:
1. A compound selected from the group consisting of:
1-(2-pyrimidyl)-3-phenyl-5-hydroxypyrazole;
1-(2-pyrimidyl)-4-benzyl-3-phenyl-5-hydroxypyrazole;
1-(2-pyrimidyl)-4-phenyl-phenyl)-3-methyl-5-hydroxypyrazole;
1-(5-chloro-6-methylamino-2-pyrimidyl)-4-ethyl-5-hydroxy pyrazole; and
1-(5-chloro-6-methylamino-2-pyrimidyl)-4-cyclohexyl-5-hydroxy pyrazole.

2. A method of combating microbes which comprises applying to such microbes or to a microbe habitat a microbicidally effective amount of a 1-[2-pyrimidyl]-5-hydroxy-pyrazole of the formula:

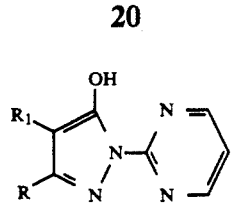

in which
R represents $C_{6-12}$-alkyl or benzyl; and
$R_1$ represents hydrogen, $C_{1-8}$-alkyl, $C_{5-7}$-cycloalkyl, $C_{1-6}$-alkoxy, $C_{1-6}$-alkoxycarbonyl, benzylmercapto, or benzyl optionally substituted by halogen, $C_{1-4}$-alkyl, halo-$C_{1-4}$-alkyl, $C_{1-4}$-alkoxy, halo-$C_{1-4}$-alkoxy, $C_{1-4}$-alkylmercapto, halo-$C_{1-4}$-alkylmercapto, nitro, or cyano.

3. A 1-[2-pyrimidyl]-5-hydroxypyrazole of the formula:

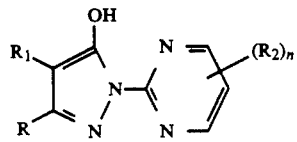

in which
R represents hydrogen; or $C_{6-10}$-alkyl optionally substituted with one or more substituents selected from the group consisting of chlorine, fluorine, $C_{1-4}$-alkoxy and $C_{1-6}$-alkoxycarbonyl;
or represents an aralkyl group selected from the group consisting of benzyl, α-methylbenzyl, α,α-dimethylbenzyl, 2-phenylethyl, α-naphthylmethyl and β-naphthylmethyl each of which is optionally substituted with a substituent selected from the group consisting of chlorine, fluorine, $C_{1-4}$-alkyl, $C_{1-4}$-alkoxy, $C_{1-4}$-alkylmercapto, halo-$C_{1-4}$-alkyl, halo-$C_{1-4}$-alkoxy, halo-$C_{1-4}$-alkylmercapto and cyano;
or represents $C_{1-12}$-alkoxy;

$R_1$ represents $C_{6-12}$-alkyl optionally substituted with one or more substituents selected from the group consisting of chlorine, fluorine, $C_{1-4}$-alkoxy and $C_{1-6}$-alkoxycarbonyl;

or an allyl group;

or a propynyl, 1-iodo-propynyl or 3,3-dimethylpropynyl group;

or $C_{5-7}$-cycloalkyl optionally substituted by $C_{1-4}$-alkyl, fluorine or chlorine;

or represents an aralkyl group selected from the group consisting of benzyl, α-methylbenzyl, α,α-dimethylbenzyl, 2-phenylethyl, α-naphthylmethyl and β-naphthylmethyl each of which is optionally substituted with a substituent selected from the group consisting of chlorine, fluorine, $C_{1-4}$-alkyl, $C_{1-4}$-alkoxy, $C_{1-4}$-alkylmercapto, halo-$C_{1-4}$-alkyl, halo-$C_{1-4}$-alkoxy, halo-$C_{1-4}$-alkylmercapto and cyano;

or represents $C_{1-12}$-alkoxy;

or represents $C_{1-4}$-alkylmercapto optionally substituted by halogen;

or benzyloxy optionally substituted by one or more substituents selected from the group consisting of halogen and $C_{1-4}$-alkyl;

or benzylmercapto optionally substituted by one or more substituents selected from the group consisting of halogen and $C_{1-4}$-alkyl;

or phenoxy optionally substituted by one or more substituents selected from the group consisting of halogen, $C_{1-4}$-alkyl, $C_{1-2}$-halogenoalkyl, cyano, nitro, trifluoromethyl and difluoromethyl;

or phenylmercapto optionally substituted by one or more substituents selected from the group consisting of halogen, $C_{1-4}$-alkyl, $C_{1-2}$-halogenoalkyl, cyano and nitro;

or methoxycarbonyl or ethoxycarbonyl;

or carboxamido, N-methylcarboxamido or N,N-dimethylaminocarboxamido;

or $R_1$ together with R forms a divalent alk(en)ylene radical which has 3 to 6 carbon atoms in the chain;

$R_2$ represents halogen, nitro, cyano, $C_{1-4}$-alkyl, $C_{1-2}$-halogenoalkyl, $C_{1-4}$-alkoxy, $C_{1-4}$-alkylmercapto, $C_{1-4}$-alkoxycarbonyl, or aminocarbonyl; and n represents 0 or an integer from 1 to 3, where $R_2$ represents identical or different radicals when n is 2 or 3.

4. A method of protecting industrial materials from attack by microbes, said method comprising applying to said industrial materials a microbicidally effective amount of a 1-[2-pyrimidyl]-5-hydroxypyrazole of the formula:

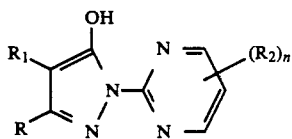

in which

R represents hydrogen; or $C_{6-10}$-alkyl optionally substituted with one or more substituents selected from the group consisting of chlorine, fluorine, $C_{1-4}$-alkoxy and $C_{1-6}$-alkoxycarbonyl;

or represents an aralkyl group selected from the group consisting of benzyl, α-methylbenzyl, α,α-dimethylbenzyl, 2-phenylethyl, α-naphthylmethyl and β-naphthylmethyl each of which is optionally substituted with a substituent selected from the group consisting of chlorine, fluorine, $C_{1-4}$-alkyl, $C_{1-4}$-alkoxy, $C_{1-4}$-alkylmercapto, halo-$C_{1-4}$-alkyl, halo-$C_{1-4}$-alkoxy, halo-$C_{1-4}$-alkylmercapto and cyano;

or represents $C_{1-12}$-alkoxy;

$R_1$ represents $C_{6-12}$-alkyl optionally substituted with one or more substituents selected from the group consisting of chlorine, fluorine, $C_{1-4}$-alkoxy and $C_{1-6}$-alkoxycarbonyl;

or an allyl group;

or a propynyl, 1-iodo-propynyl or 3,3-dimethylpropynyl group;

or $C_{5-7}$-cycloalkyl optionally substituted by $C_{1-4}$-alkyl, fluorine or chlorine;

or represents an aralkyl group selected from the group consisting of benzyl, α-methylbenzyl, α,α-dimethylbenzyl, 2-phenylethyl, α-naphthylmethyl and β-naphthylmethyl each of which is optionally substituted with a substituent selected from the group consisting of chlorine, fluorine, $C_{1-4}$-alkyl, $C_{1-4}$-alkoxy, $C_{1-4}$-alkylmercapto, halo-$C_{1-4}$-alkyl, halo-$C_{1-4}$-alkoxy, halo-$C_{1-4}$-alkylmercapto and cyano;

or represents $C_{1-12}$-alkoxy;

or represents $C_{1-4}$-alkylmercapto optionally substituted by halogen;

or benzyloxy optionally substituted by one or more substituents selected from the group consisting of halogen and $C_{1-4}$-alkyl;

or benzylmercapto optionally substituted by one or more substituents selected from the group consisting of halogen and $C_{1-4}$-alkyl;

or phenoxy optionally substituted by one or more substituents selected from the group consisting of halogen, $C_{1-4}$-alkyl, $C_{1-2}$-halogenoalkyl, cyano, nitro, trifluoromethyl and difluoromethyl;

or phenylmercapto optionally substituted by one or more substituents selected from the group consisting of halogen, $C_{1-4}$-alkyl, $C_{1-2}$-halogenoalkyl, cyano and nitro;

or methoxycarbonyl or ethoxycarbonyl;

or carboxamido, N-methylcarboxamido or N,N-dimethylaminocarboxamido;

or $R_1$ together with R forms a divalent alk(en)ylene radical which has 3 to 6 carbon atoms in the chain;

$R_2$ represents halogen, nitro, cyano, $C_{1-4}$-alkyl, $C_{1-2}$-halogenoalkyl, $C_{1-4}$-alkoxy, $C_{1-4}$-alkylmercapto, $C_{1-4}$-alkoxycarbonyl, or aminocarbonyl; and n represents 0 or an integer from 1 to 3, where $R_2$ represents identical or different radicals when n is 2 or 3.

5. A microbicidal composition comprising a microbicidally effective amount of a compound according to claim 3 and a diluent.

6. A microbicidal composition comprising a microbicidally effective amount of a compound according to claim 1 and a diluent.

7. A method of combating microbes which comprises applying to such microbes or to a microbe habitat a microbicidally effective amount of a 1-(2-pyrimidyl)-5-hydroxy-pyrazole according to claim 1.

* * * * *